US008754260B2

(12) United States Patent
Cote et al.

(10) Patent No.: US 8,754,260 B2
(45) Date of Patent: Jun. 17, 2014

(54) METHOD FOR PREPARING FLUOROACYLATED ARYLAMINE

(71) Applicant: Xerox Corporation, Norwalk, CT (US)

(72) Inventors: Adrien P Cote, Clarkson (CA); Amanda L Bongers, Ottawa (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/682,767

(22) Filed: Nov. 21, 2012

(65) Prior Publication Data

US 2014/0142339 A1     May 22, 2014

(51) Int. Cl.
*C07C 241/00*     (2006.01)
*C07C 243/00*     (2006.01)
*C07C 249/00*     (2006.01)
*C07C 251/00*     (2006.01)
*C07C 211/00*     (2006.01)

(52) U.S. Cl.
USPC ............................................. 564/314; 564/309

(58) Field of Classification Search
None
See application file for complete search history.

(56) References Cited

U.S. PATENT DOCUMENTS 5,202,408 A     4/1993     Yanus et al.
7,652,148 B1     1/2010     Cote et al.

FOREIGN PATENT DOCUMENTS

SU     355157     *     1/1973

OTHER PUBLICATIONS

Armarego, Purification of Laboratory Chemicals, 5th edition, front matter and pp. 1-17, 2003.*
SU 355157 Derwent abstract 2 pages.*

* cited by examiner

*Primary Examiner* — Clinton Brooks
(74) *Attorney, Agent, or Firm* — MDIP LLC

(57) ABSTRACT

A method for making fluoroacyl arylamines is disclosed.

19 Claims, No Drawings

METHOD FOR PREPARING FLUOROACYLATED ARYLAMINE

FIELD

A novel method for synthesizing fluoroacylated arylamines is provided. The method is undemanding with good product yield. The compounds have favorable electroactivity and are suitable for organic electronic applications.

BACKGROUND

Arylamines are used in organic electronics applications including use in photoreceptors, thin film transistors (TFT), photovoltaic (PV) cells, light emitting diodes (LEDs) etc. In the electrophotographic imaging field, the photoactive portions of components can be composed of organic materials, such as, the fluoacylated arylamines of interest, which act as photoreceptors for temporarily forming an image in the form of a pattern of charges on the photoreceptor.

Arylamines and arylamine derivatives are known but none comprises a fluoroacyl moiety or the altered electronic properties of the compounds described herein. The synthesis of the compounds of interest as provided herein does not employ a Friedel-Crafts acylation reaction using a Lewis acid, such as, aluminum trichloride, to activate the acyl entities for addition to arylamine phenyl rings.

SUMMARY

Disclosed herein is a method for synthesizing fluoroacyl arylamines.

In embodiments, fluoroacyl arylamines are prepared without Lewis acids and a Friedel-Crafts acylation reaction as is normally practiced in the art. Fluoroacyl arylamines are obtained from an arylamine and a trifluoroacyl-donating reagent, such as, trifluoroacetic anyhydride, compounds containing a trifluoroacetic anhydride group and so on, in a single reaction scheme without using a Lewis acid.

Those and other features and advantages of various embodiments of materials, devices, systems and/or methods relating to making and using certain fluoroacylated arylamines of interest are described in or are apparent from the following description.

DESCRIPTION

While not wishing to be bound by any particular theory, the one or more fluoroacyl groups added to an arylamine as produced by the present method of interest, impart new electronic properties and configurations to conventional arylamine electronic material. Hence, the arylamines carrying one or more fluoroacyl groups have different and/or improved properties, such as, charge transport properties, and are useful for a number of different electronic and other industrial uses.

For example, a fluoroacyl arylamine of interest can be used as a charge transport molecule in a photoreceptor. The one or more fluoroacyl moieties alter the charge distribution of the parent arylamine bestowing a fluoroacyl arylamine with different electronic, such as, charge transport, properties from the base arylamine.

The fluoroacyl arylamine may be formed into a thin coating alone or by using a suitable film-forming material to result, for example, in a charge transport layer (CTL). The film-forming material can be a transparent organic polymer or non-polymeric material capable of supporting the injection of photogenerated holes or electrons and capable of allowing the transport of the holes/electrons through the CTL to selectively discharge the charge on the surface of the imaging device component, such as, a photoreceptor. The CTL containing the fluoroacyl arylamine exhibits substantial optical transparency with insignificant light absorption and negligible charge generation when exposed to a wavelength of light useful in, for example, photocopying devices, e.g., from about 400 nm to about 900 nm.

Any suitable and conventional technique may be used to mix and thereafter to apply the CTL coating mixture to a photoreceptor under construction. Typical application techniques include spraying, dip coating, roll coating, wire wound rod coating and the like. Drying of the deposited coating may be obtained by any suitable conventional technique, such as, oven drying, infrared drying, air drying and the like.

The term, "arylamine," refers, for example, to moieties containing both aryl and amine groups. Arylamines can have the structure Ar—NRR', in which Ar represents an aryl group and R and R' are groups that independently may be selected from hydrogen and substituted or unsubstituted alkyl, alkenyl, aryl and other suitable hydrocarbons and/or functional groups. The term, "triarylamine," refers, for example, to arylamine compounds having the general structure NArAr'Ar", in which Ar, Ar" and A" represent independently selected aryl groups, which may be substituted, functionalized and so on.

In an embodiment, an arylamine substrate of interest comprises the structure:

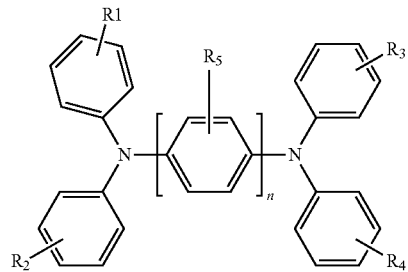

where $R_1$, $R_2$, $R_3$, $R_4$ and $R_5$ may be located at any site on a phenyl group; and can be one or more hydrogen atoms; a halogen; a hydrocarbon, which can be saturated, substituted or contain a heteroatom, such as, N, O, S and so on, of 1 to about 8 carbon atoms, for example, alkyl, alkenyl, aryl, hydroxyl, oxyalkyl and so on; or a functional group comprising a reactive moiety or site; and n is 0, 1, 2 or 3. A functional group can comprise a hydroxyl group, a carbonyl group, a halogen, an amino group and so on as a design choice.

The trifluoroacyl-donating reagent can be an acid, an anhydride thereof and so on. An example of an anhydride is one with the formula:

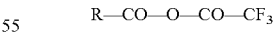

R—CO—O—CO—CF$_3$ where R may be $CF_3$, alkyl, aryl, substituted alkyl or substituted aryl, where the substitutions may be halogen, hydroxy or nitro, wherein the alkyl or aryl may have between 1 and about 8 carbon atoms.

The synthesis reaction occurs in a suitable solution or solvent which dissolves both the trifluoroacyl-donating reagent, such as, a trifluoro anhydride, such as, trifluoroacetic anhydride, and the arylamine reagent, and is inert to the reaction between the two substrates or reactants. The liquid reaction mixture may comprise one compound or a mixture of two or more compounds. In embodiments, the reaction solution is not miscible significantly with water so that the resulting product may be isolated by phase separation. Suitable liquids include hydrocarbons, ethers, long chain alcohols, hydrocarbons derivatized by halogens, ethers or long chain alcohols and mixtures thereof. Compatible liquids with higher boiling points may be used to allow the reaction to occur at a higher temperature. Examples include halogenated hydrocarbons, aliphatic nitriles, alkanes and so on, such as, but not limited to, dicholoromethane, hexane and acetonitrile.

In an embodiment, the arylamine may be structure A or B:

A:

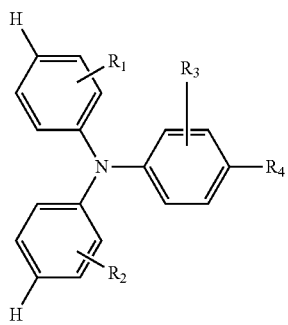

or B:

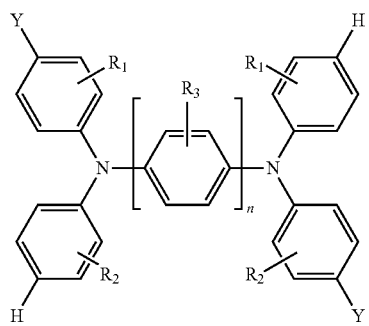

wherein Y is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; $R_1$, $R_2$ and $R_3$ each is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; $R_4$ is hydrogen, $C_1$-$C_5$ alkyl, $C_3$-$C_7$ cyclic alkyl, hydroxy, ω-hydroxy substituted $C_2$-$C_8$ alkyl, halogen or aryl optionally substituted with $C_1$-$C_5$ alkyl and n is 0, 1, 2 or 3.

In another embodiment, structure A may be:

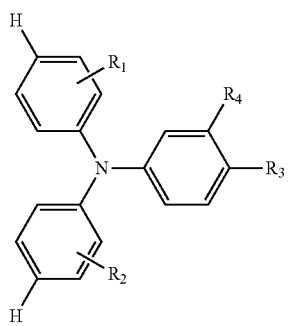

wherein $R_1$, $R_2$, $R_3$ and $R_4$ are as defined above.

In another embodiment, structure B has a structure:

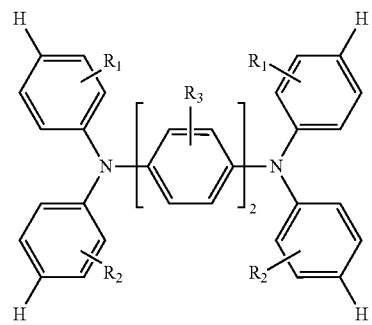

wherein $R_1$, $R_2$ and $R_3$ are as defined above.

Alternatively, compound B has a structure:

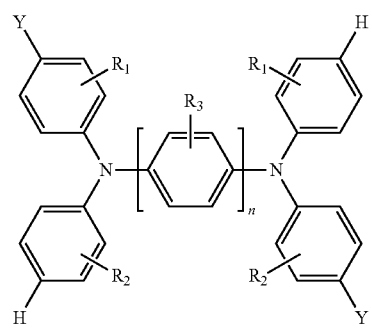

wherein Y is methyl, and n, $R_1$, $R_2$ and $R_3$ are as defined above.

In another embodiment, the arylamine is selected from the group consisting of:

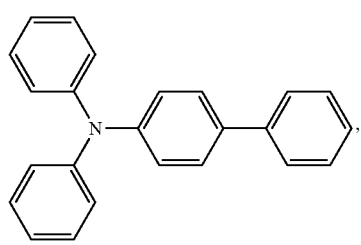

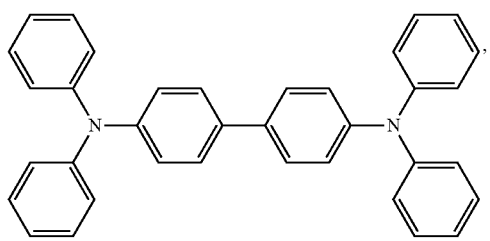

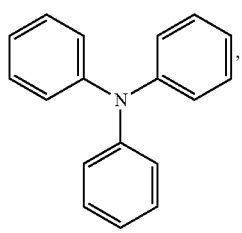
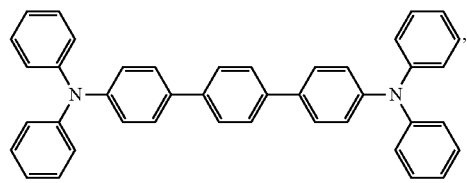
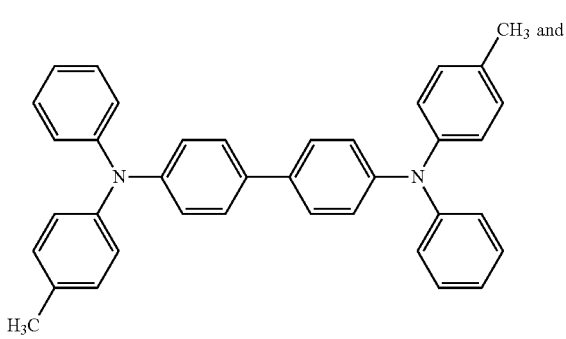
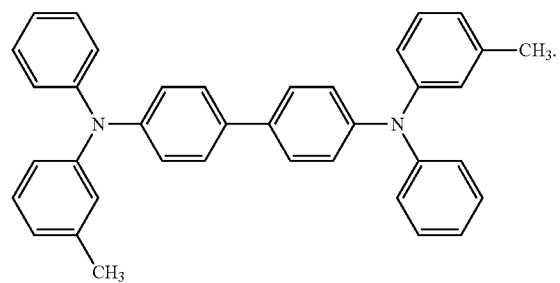
In embodiments, a fluoroacyl arylamine of interest comprises:
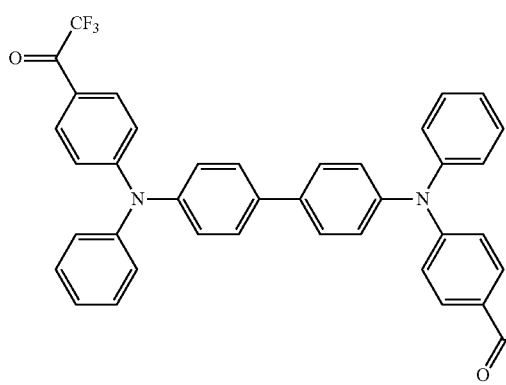
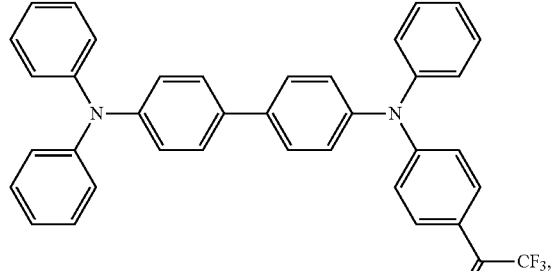
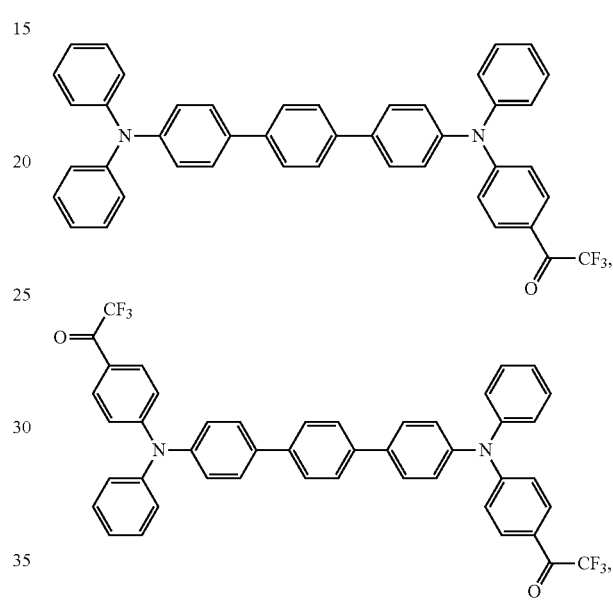
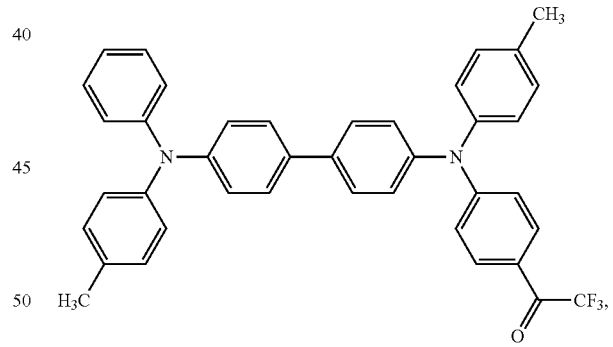
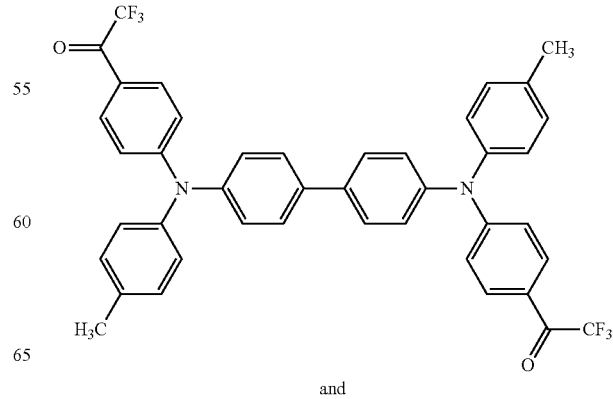
and -continued

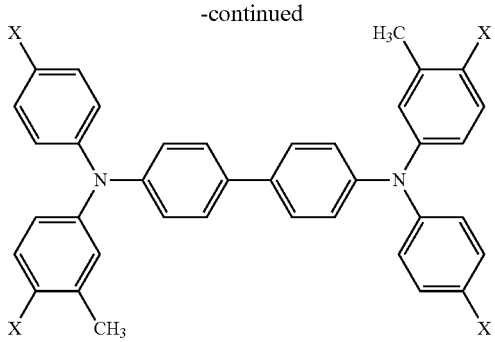

wherein, X is a fluoroacyl group or hydrogen and the number of fluoroacyl groups ranges from 1 to 4;

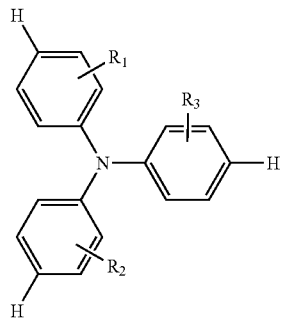

wherein $R_1$, $R_2$ and $R_3$ are as defined above; and at least one ring comprises at least one fluoroacyl moiety;

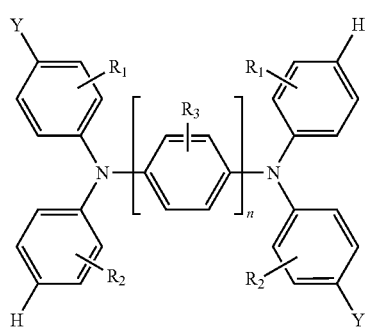

wherein n, Y, $R_1$, $R_2$ and $R_3$ are as defined above; and at least one ring comprises at least one fluoroacyl moiety;

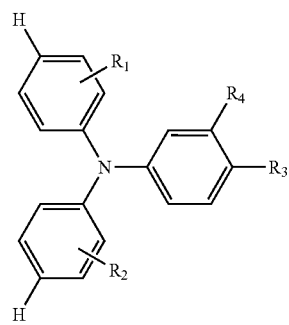

wherein $R_1$, $R_2$, $R_3$ and $R_4$ are as defined above, and one or more rings comprise at least one fluoroacyl moiety; or

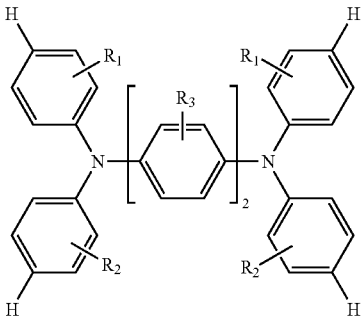

wherein $R_1$, $R_2$ and $R_3$ are as defined above, and one or more of the rings comprise at least one fluoroacyl moiety.

In embodiments, the temperature and pressure of the reaction are such that the reaction mixture remains in liquid form and continues to dissolve all of the chemical reactants and products. The conditions may vary with the reactants and/or liquid reagent(s) used.

The reaction may occur in a reactor maintained at room temperature or slightly higher. In embodiments, the reaction temperature can be from about 25° C. to about 90° C., from about 30° C. to about 80° C., from about 40° C. to about 70° C. Higher temperatures may be used with suitable reagents which do not become overly volatile at those elevated temperatures. Higher temperatures may be used to increase the rate of reaction. To reduce liquid loss or to facilitate reaction kinetics, the reaction may occur under reflux, occur in closed conditions or under pressure, for example.

The reaction time may vary with the temperature and individual starting materials. The more reactive the trifluoroacyl-donating compound and/or the higher the temperature, reaction time may be abbreviated. The reaction time also may vary with the particular arylamine substrate and the number and location of fluoroacyl moieties that are incorporated in the product.

During the reaction, progress may be monitored by observation of reaction color, reaction turbidity and so on, which parameters can be monitored visually or using an appropriate sensor. A sample may be removed periodically and analyzed, for example, by HPLC or other analytic method, or a sample may flow from the main reaction vessel by or through a sensor or other monitoring device, such as, a spectrophotometer.

After the reaction is completed, the final product resembles the arylamine substrate but with one or more fluoroacyl moieties attached to one or more of the pendant aryl moieties. In embodiments, the fluoroacyl moiety can be attached in the para position, however, the fluoroacyl residue can be located at other positions on an aryl ring. Also, any one aryl group may contain more than one fluoroacyl group. An acid byproduct also may be produced from an acid anhydride reagent.

The final fluoroacyl arylamine product can be separated by removal, precipitation and/or inactivation of any reagent or byproduct, such as, an acid byproduct when using an anhydride, such as, by neutralization. The solution also can be removed, such as, by evaporation and/or precipitating the product. Acid byproducts, such as, trifluoroacetic acid when an anhydride is used, can be dissolved in aqueous solutions and may be washed with aqueous or ionic liquids to be separated from the fluoroacyl arylamine-containing solution. The final fluoroacyl arylamine product also may be dried to remove residual liquid reactants and water, for example, by vacuum and/or heat. Complete removal of liquid reactants and reagents and/or water may be determined when the weight remains constant.

Because of the reaction scheme and kinetics, little may need to be done to purify the fluoroacyl arylamine compound from the reaction mixture, although additional separation, filtration and/or purification processes can be conducted, as desired, to a desired purity level or as needed, for example, based on the starting reagents. For example, the desired fluoroacylated arylamine product can be subjected to conventional organic washing steps, can be separated, can be decolorized (if necessary), treated with known absorbents (such as silica, alumina, carbon, clays and the like, if necessary) and the like. The final product can be isolated, for example, by a suitable precipitation or crystallization procedure. Such procedures are conventional and will be apparent to those skilled in the art.

The resulting fluoroacylated arylamine may have 1, 2 or more fluoroacyl moieties attached to any of the aromatic rings at any position. Certain positions of attachment may be selected as a design choice from a reaction standpoint, others may be synthesized by adjusting the reaction conditions and trifluoroacyl-donating molecule. The molar amount of trifluoroacyl-donating molecule in the reaction can determine the number of fluoroacyl moieties attached to the arylamine core structure.

The fluoroacylated arylamine can be used as a final product or can be further processed and/or reacted to provide other compounds for similar or different uses. For example, the fluoroacylarylamine may be used in a composition, for example, as a charge transport molecule in a CTL of an electrophotographic imaging member. The compounds of interest comprise one or more reactive carbonyl groups or can be synthesized to comprise other functional or reactive groups. Hence, the compounds of interest can be used as reagent for producing other compounds, polymers and so on, practicing materials and methods known in the art as a design choice. Hence, the fluoroacyl arylamine molecules can be used to produce polymers and copolymers resulting from chemical reaction(s) to add additional reactive moieties or functional groups to the fluoroacyl arylamine core, where the functional groups can react in a polymerization reaction; polymerization of fluoroacyl arylamine molecules; further derivatization of fluoroacyl arylamines; using a fluoroacyl arylamine as a starting material to synthesize another novel compound retaining the basic fluoroacyl arylamine structure; and so on.

The reaction of interest produces product in high yield, high purity or both without byproduct (other than the intended acid byproduct when an anhydride is used) or starting material contamination. In bench top laboratory experiments, yields of about 70% or more are obtained with purities greater than about 90%.

The synthesis reaction of interest does not require or use a Lewis acid or other metal, which later needs to be removed or which can interfere with purification of the fluoroacyl arylamine product.

Traditionally, multiple chemical reactions were required to synthesize different arylamines. On the other hand, the reaction of interest may be done simply, for example, in a single vessel, as a one-step reaction or both without need for multiple reactions, multiple reagent introductions, complicated purification schemes and so on, which incurs cost and make product purity more difficult to obtain.

The final chemical structure of the fluoroacyl arylamine product may be determined by, for example, HPLC, LC/MS, $^1$H NMR, $^{19}$F NMR, FT-IR, elemental analysis, crystallography and so on.

The disclosure is not limited to particular embodiments described herein, and some components and processes may be varied by one of skill, based on the disclosure. The terminology used herein is for the purpose of describing particular embodiments only and is not intended to be limiting.

Various aspects of the embodiments of interest now will be exemplified in the following non-limiting examples.

EXAMPLES

Example 1

Synthesis of DFA-Tetraphenylenebiphenyldiamine

To a 100 ml flask containing 30 ml DCM (dichloromethane) were added 2.44 g (5.0 mmol, 1.0 equivalent) of tetraphenylenebiphenyldiamine (TBD) to yield a beige slurry. Then, 5.6 ml (40 mmol, 8.0 equivalents) of TFAA (trifluoroacetic anhydride) were poured into the mixture and the flask equipped with a reflux condenser. The mixture was heated to reflux (40° C.), the reactant dissolving to form a dark brown solution. The reaction was stirred for 72 hours at the reflux temperature.

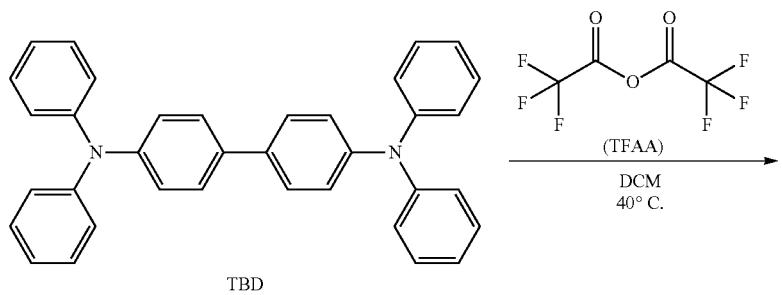

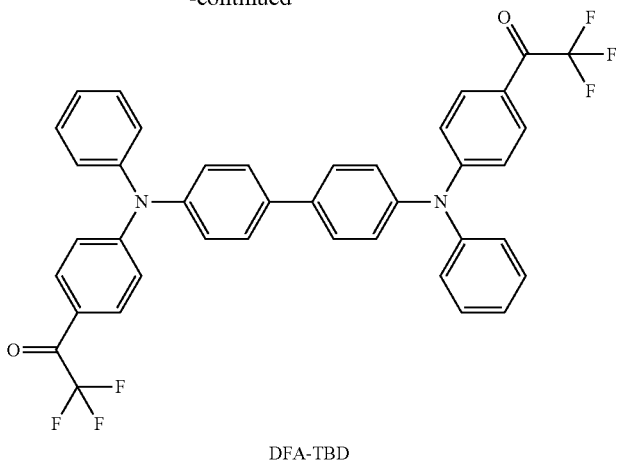

DFA-TBD

When the reaction was complete (determined by HPLC to be >99% conversion), the mixture was cooled to room temperature then diluted with 30 ml DCM. The solution was then poured into 25 ml of stirring $H_2O$. The organic layer was isolated and washed with two 10 ml portions of a 1/1 mixture of $H_2O$/saturated $NaHCO_3$ and one 10 ml portion of a sodium chloride buffer, such as a saturated NaCl solution. The aqueous wash which contains the acid byproduct was removed. That solution has a pH approaching neutral. The DCM solution then was dried with $Na_2SO_4$ and removed by evaporation to yield di(trifluoroacyl) (DFA)-tetraphenylenebiphenyldiamine as 1.2 g (70%) of a golden yellow solid. The chemical structure was confirmed by nuclear magnetic resonance with $^1$H NMR (300 MHz, $CH_2Cl_2$-d2) δ 7.93 (d, J=8.4 Hz, 4H), 7.60 (d, J=8.4 Hz, 4H), 7.42 (dd, J=7.3 Hz, 2H), 7.27-7.24 (12H), 7.04 (d, J=9.0 Hz, 4H). $^{19}$F NMR (300 MHz, $CH_2Cl_2$-d2) δ 71.2 (s, 6F).

Example 2

Synthesis of DFA-Para-methyl tetraphenylenebiphenyldiamine

To a 100 ml flask containing 30 ml DCM were added 2.58 g (5.0 mmol, 1.0 equivalent) of para-methyl tetraphenylenebiphenyldiamine (pTBD) to yield a beige slurry. Then, 2.8 ml (20 mmol, 8.0 equivalents) of TFAA were poured into the mixture and the flask equipped with a reflux condenser. The mixture was heated to reflux (40° C.), the reagent dissolving to form a dark red-brown solution. The reaction was stirred for 48 hours at the reflux temperature.

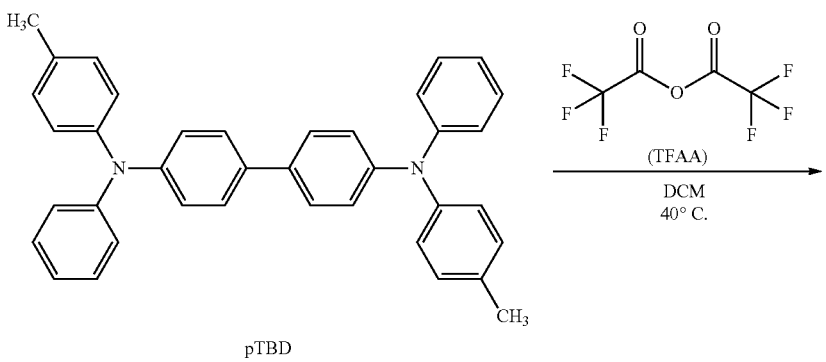

pTBD

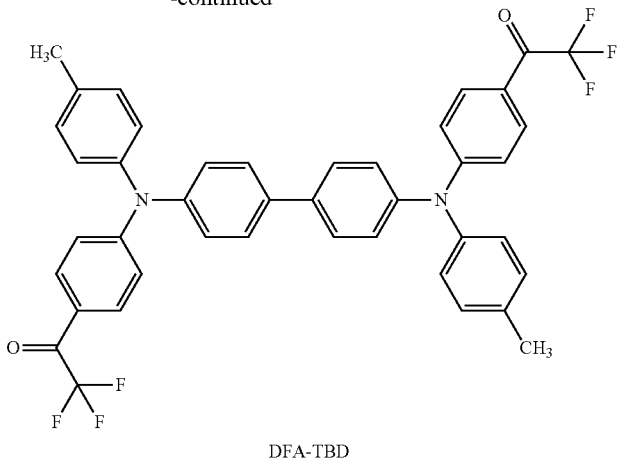

DFA-TBD

When the reaction was complete (determined by HPLC to be >99% conversion), the mixture was cooled to room temperature then diluted with 30 ml DCM. The solution was then poured into 25 ml of stirring $H_2O$. The organic layer was isolated and washed with two 10 ml portions of a 1/1 mixture of $H_2O$/saturated $NaHCO_3$ and one 10 ml portion of NaCl buffer. The neutral pH aqueous wash which contains the acid byproduct was removed. The DCM solution then was removed by evaporation to yield DFA-product as 3 g (85%) of amber solid. The chemical structure was confirmed by nuclear magnetic resonance with $^1H$ NMR (300 MHz, $CH_2Cl_2$-d2) δ 7.91 (d, J=8.4 Hz, 4H), 7.58 (d, J=8.4 Hz, 4H), 7.27-7.10 (12H), 7.01 (d, J=9.3 Hz, 4H), 2.40 (s, 6H). $^{19}F$ NMR (300 MHz, $CH_2Cl_2$-d2) δ 71.1 (s, 6F).

It will be appreciated that various of the above-discussed and other features and functions, (or alternatives thereof) desirably may be combined into other different systems or applications. Also, that various presently unforeseen or unanticipated alternatives, modifications, variations or improvements therein may be subsequently made by those skilled in the art also are intended to be encompassed by the following claims.

All references cited herein are herein incorporated by reference in entirety.

The invention claimed is:

1. A method of producing a fluoroacyl arylamine comprising contacting an arylamine and a fluoroacyl-donating compound in a mixture and isolating said fluoroacyl arylamine from said mixture, wherein the fluoroacyl-donating compound is R—CO—O—CO—$CF_3$, wherein R is $CF_3$, alkyl, aryl, substituted alkyl or substituted aryl, where the substitutions may be halogen, hydroxy or nitro, wherein the alkyl or aryl has between 1 and about 8 carbon atoms; and wherein the fluoroacyl arylamine comprises:

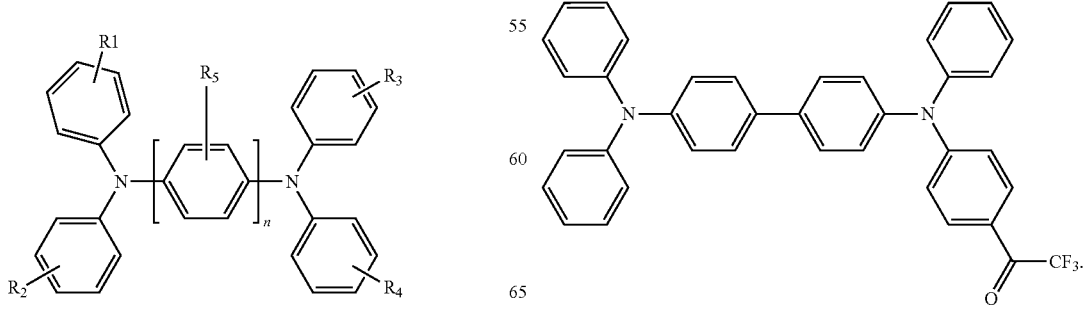

wherein each of $R_1$, $R_2$, $R_3$, $R_4$ and $R_5$ is located at any site on an aryl group; and is one or more hydrogen atoms; a halogen, a hydrocarbon of 1 to about 8 carbon atoms, which can be substituted and can comprise a heteroatom, or a functional group; n is 1, 2 or 3; and at least one ring comprises at least one fluoroacyl group.

2. The method of claim 1, wherein said fluoroacyl arylamine comprises:

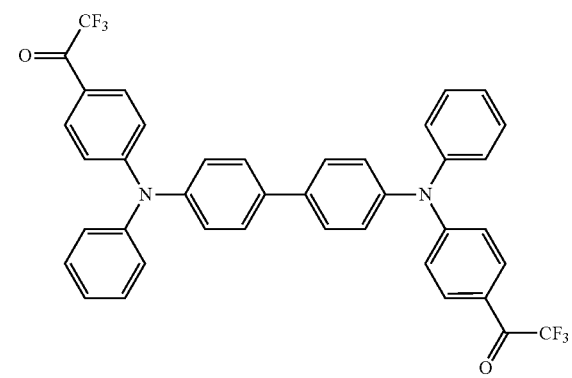 [SMILES: O=C(c1ccc(N(c2ccccc2)c2ccc(-c3ccc(N(c4ccccc4)c4ccc(C(=O)C(F)(F)F)cc4)cc3)cc2)cc1)C(F)(F)F]

or

3. The method of claim 1, wherein said fluoroacyl arylamine comprises,

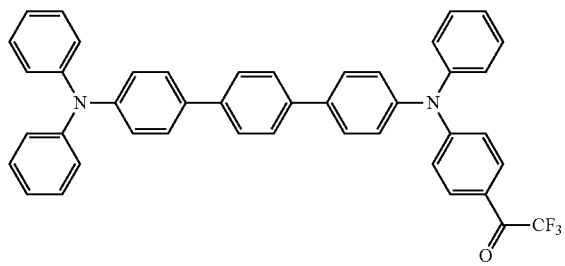 [SMILES: O=C(c1ccc(N(c2ccccc2)c2ccc(-c3ccc(-c4ccc(N(c5ccccc5)c5ccccc5)cc4)cc3)cc2)cc1)C(F)(F)F]

or

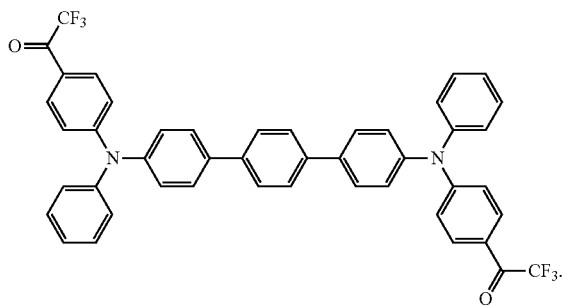 [SMILES: O=C(c1ccc(N(c2ccccc2)c2ccc(-c3ccc(-c4ccc(N(c5ccccc5)c5ccc(C(=O)C(F)(F)F)cc5)cc4)cc3)cc2)cc1)C(F)(F)F]

4. The method of claim 1, wherein said fluoroacyl arylamine comprises:

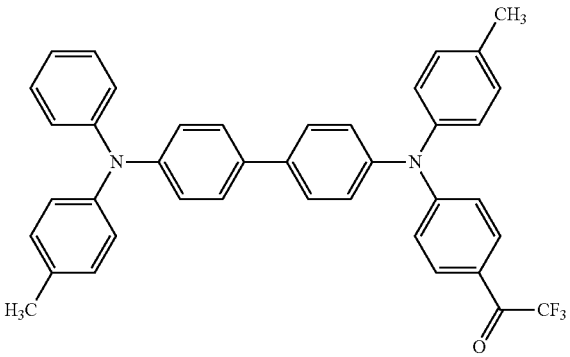 [SMILES: Cc1ccc(N(c2ccccc2)c2ccc(-c3ccc(N(c4ccc(C)cc4)c4ccc(C(=O)C(F)(F)F)cc4)cc3)cc2)cc1]

or

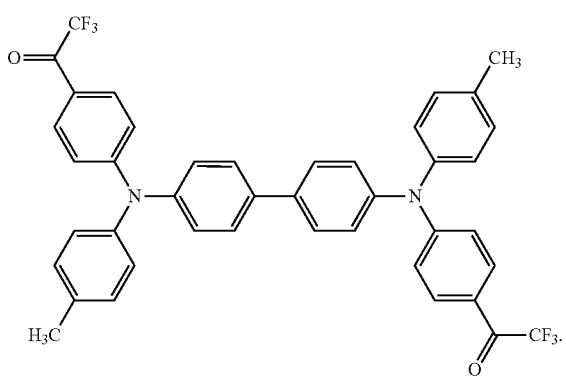 [SMILES: Cc1ccc(N(c2ccc(C(=O)C(F)(F)F)cc2)c2ccc(-c3ccc(N(c4ccc(C)cc4)c4ccc(C(=O)C(F)(F)F)cc4)cc3)cc2)cc1]

5. The method of claim 1, wherein said fluoroacyl arylamine comprises,

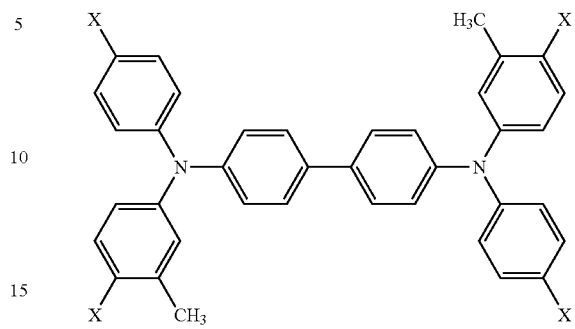

wherein, X is a fluoroacyl group or hydrogen and the number of fluoroacyl groups ranges from 1 to 4.

6. The method of claim 1, wherein said contacting comprises a solution immiscible with water.

7. The method of claim 6, wherein said solution comprises dicholoromethane.

8. The method of claim 6, comprising isolating said fluoroacyl arylamine from said solution immiscible with water.

9. The method of claim 1, wherein said fluoroacyl-donating compound comprises a trifluoro anhydride or a trifluoroacetic anhydride.

10. The method of claim 1, wherein said contacting occurs at a temperature from about 25° C. to about 90° C.

11. The method of claim 1, wherein said contacting occurs under reflux.

12. The method of claim 1, wherein said isolating comprises contacting said mixture with a solution comprising water.

13. A method of producing a fluoroacyl arylamine comprising contacting an arylamine and a fluoroacyl-donating compound in a mixture and isolating said fluoroacyl arylamine from said mixture, wherein the fluoroacyl-donating compound is R—CO—O—CO—CF$_3$, wherein R is CF$_3$, alkyl, aryl, substituted alkyl or substituted aryl, where the substitutions may be halogen, hydroxy or nitro, wherein the alkyl or aryl has between 1 and about 8 carbon atoms; and wherein said fluoroacyl arylamine comprises

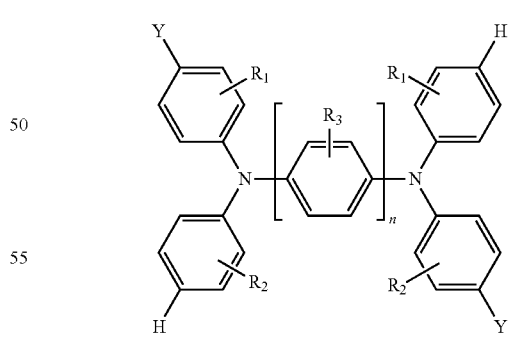

wherein Y is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; $R_1$, $R_2$, and $R_3$ each is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; n is 0, 1, 2 or 3; and at least one ring comprises at least one fluoroacyl moiety.

14. The method of claim 13, wherein said fluoroacyl arylamine comprises:

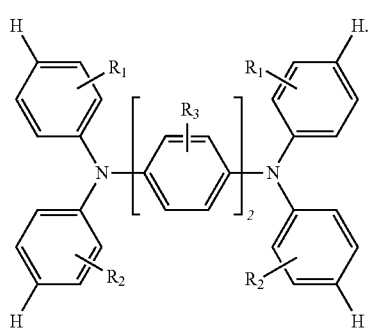

15. The method of claim 13, comprising said fluoroacyl arylamine, wherein Y is methyl.

16. The method of claim 13, wherein said fluoroacyl-donating compound comprises a trifluoroacetic anhydride or a trifluoro anhydride.

17. The method of claim 13, wherein said contacting comprises a solution immiscible with water, wherein the solution optionally comprises dicholoromethane.

18. The method of claim 13, wherein said contacting occurs at a temperature from about 25° C. to about 90° C., wherein said contacting optionally occurs under reflux.

19. The method of claim 13, wherein said arylamine comprises:

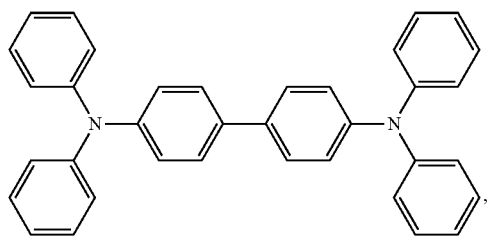

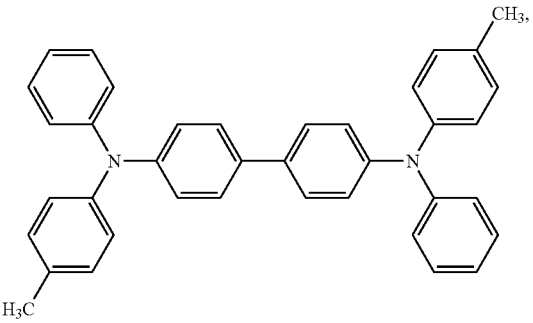

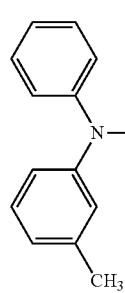

or

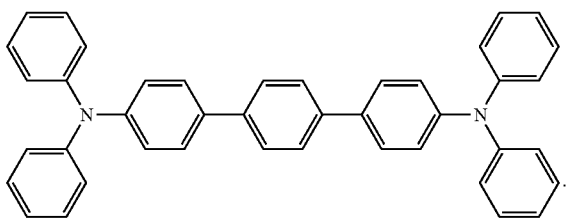

* * * * *